US008592780B2

(12) United States Patent
Iguchi

(10) Patent No.: US 8,592,780 B2
(45) Date of Patent: Nov. 26, 2013

(54) QUANTUM-YIELD MEASUREMENT DEVICE

(75) Inventor: Kazuya Iguchi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 13/988,788

(22) PCT Filed: Aug. 31, 2011

(86) PCT No.: PCT/JP2011/069836
§ 371 (c)(1),
(2), (4) Date: May 22, 2013

(87) PCT Pub. No.: WO2012/073567
PCT Pub. Date: Jun. 7, 2012

(65) Prior Publication Data
US 2013/0248737 A1    Sep. 26, 2013

(30) Foreign Application Priority Data
Nov. 29, 2010  (JP) ................................. 2010-264831

(51) Int. Cl.
*G01J 5/58*    (2006.01)
(52) U.S. Cl.
USPC .................................... 250/458.1; 250/459.1
(58) Field of Classification Search
USPC ..................................................... 250/458.1
See application file for complete search history.

(56) References Cited

U.S. PATENT DOCUMENTS

| 4,876,183 A  * | 10/1989 | Miyasaka et al. ............. 430/567 |
| 2004/0233428 A1* | 11/2004 | Hart et al. ..................... 356/319 |
| 2010/0102238 A1* | 4/2010 | Kanazawa et al. ........ 250/363.01 |
| 2010/0108869 A1* | 5/2010 | Iguchi et al. .................. 250/228 |

FOREIGN PATENT DOCUMENTS

| JP | 7-83828 A | 3/1995 |
| JP | 7-120323 A | 5/1995 |
| JP | 10-73486 A | 3/1998 |
| JP | 2007-086031 A | 4/2007 |
| JP | 2009-074866 A | 4/2009 |
| JP | 2010-151632 A | 7/2010 |

OTHER PUBLICATIONS

Christian Würth et al., "Evaluation of a Commercial Integrating Sphere Setup for the Determination of Absolute Photoluminescence Quantum Yields of Dilute Dye Solutions," Applied Spectroscopy, Jul. 2010, pp. 733-741, vol. 64, No. 7.

* cited by examiner

*Primary Examiner* — Marcus Taningco
(74) *Attorney, Agent, or Firm* — Drinker Biddle & Reath LLP

(57) ABSTRACT

A quantum-yield measurement device 1 comprises a dark box 5; a light generation unit, having a light exit part 7, for generating the pumping light L1; a light detection unit, having a light entrance part 11, for detecting light to be measured L2; an integrating sphere 14, having a light entrance opening 15 for the light L1 to enter and a light exit opening 16 for the light L2 to exit; and a movement mechanism 30 for moving the sphere 14 within the box 5 such that a container 3 attains each of a first state of being located inside of the sphere 14 and a second state of being located outside of the sphere 14 and, causing the opening 15 and opening 16 to oppose the part 7 and part 11, respectively, in the first state.

7 Claims, 9 Drawing Sheets

Fig.8
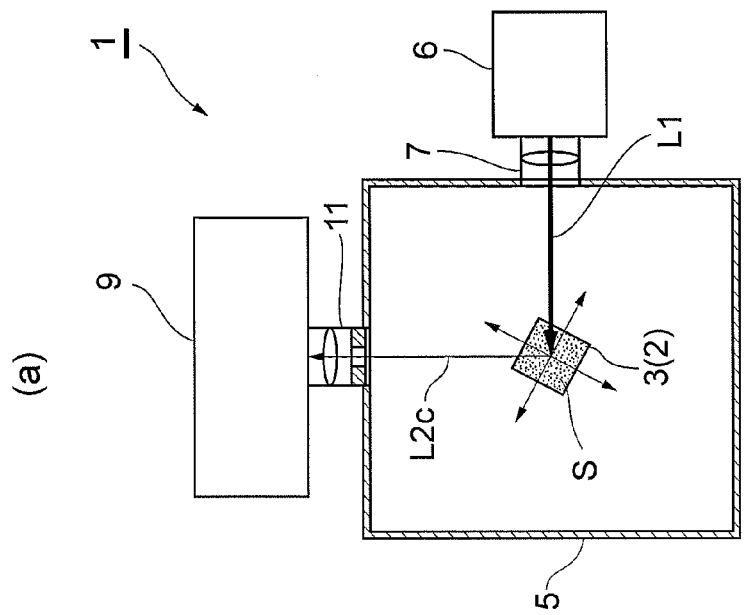
(a)
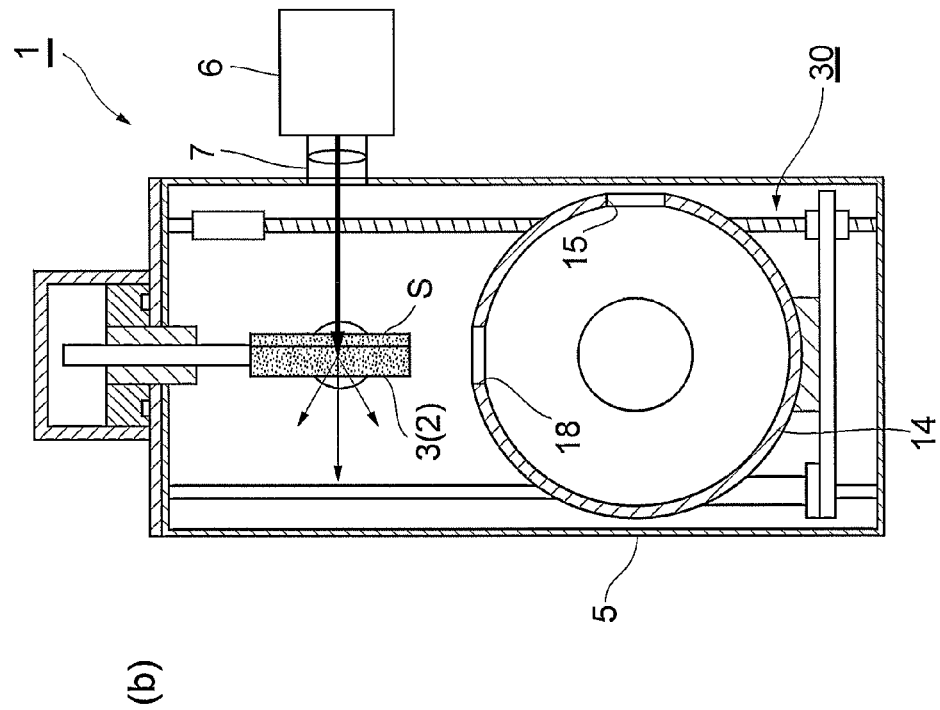
(b)

QUANTUM-YIELD MEASUREMENT DEVICE

TECHNICAL FIELD

The present invention relates to a quantum-yield measurement device for measuring a quantum yield of a light-emitting material and the like by using an integrating sphere.

BACKGROUND ART

Known as a conventional quantum-yield measurement device is a technique which irradiates a sample such as a light-emitting material with pumping light, employs an integrating sphere to cause therein multiple reflections of a fluorescence emitted from the sample, and detects thus reflected light, so as to measure a quantum yield (ratio of "the number of photons of the fluorescence emitted from the light-emitting material" to "the number of photons of the pumping light absorbed by the light-emitting material") of the sample (see, for example, Patent Literatures 1 to 3).

When the sample is optically absorptive with respect to the fluorescent component in such a technique, there is a case where a part of the fluorescence is absorbed by the sample (which phenomenon will be referred to as "reabsorption" hereinafter). In such a case, the number of photons will be calculated smaller than the true number (i.e., the number of photons of the fluorescence actually emitted from the light-emitting material). It has therefore been proposed to use a fluorometer separately to measure the intensity of a fluorescence emitted from the sample in a state generating no reabsorption and correct according thereto the number of photons of the former fluorescence, so as to determine the quantum yield (see, for example, Non Patent Literature 1).

CITATION LIST

Patent Literature

Patent Literature 1: Japanese Patent Application Laid-Open No. 2007-086031
Patent Literature 2: Japanese Patent Application Laid-Open No. 2009-074866
Patent Literature 3: Japanese Patent Application Laid-Open No. 2010-151632

Non Patent Literature

Non Patent Literature 1: Christian Wurth and 7 others, "Evaluation of a Commercial Integrating Sphere Setup for the Determination of Absolute Photoluminescence Quantum Yields of Dilute Dye Solutions," APPLIED SPECTROSCOPY, (USA) Volume 64, Nov. 7, 2010, p. 733-741.

SUMMARY OF INVENTION

Technical Problem

As mentioned above, cumbersome operations such as using a fluorometer separately from a device equipped with an integrating sphere are required for accurately measuring the quantum yield of the sample by using the integrating sphere.

It is therefore an object of the present invention to provide a quantum-yield measurement device which can measure the quantum yield of the sample accurately and efficiently.

Solution to Problem

The quantum-yield measurement device in accordance with one aspect of the present invention is a quantum-yield measurement device for measuring a quantum yield of a sample by irradiating a sample container of a sample cell for containing the sample with pumping light and detecting light to be measured emitted from at least one of the sample and sample container, the device comprising a dark box for arranging therein the sample container; a light generation unit, having a light exit part connected to the dark box, for generating the pumping light; a light detection unit, having a light entrance part connected to the dark box, for detecting the light to be measured; an integrating sphere, arranged within the dark box, having a light entrance opening for the pumping light to enter and a light exit opening for the light to be measured to exit; and a movement mechanism for moving the integrating sphere such that the sample container attains each of a first state of being located inside of the integrating sphere and a second state of being located outside of the integrating sphere, and causing the light entrance opening to oppose the light exit part and causing the light exit opening to oppose the light entrance part, in the first state.

In this quantum-yield measurement device, the movement mechanism moves the integrating sphere within the dark box such that the sample container of the sample cell attains each of the first state of being located inside of the integrating sphere and the second state of being located outside of the integrating sphere. This makes it possible to detect a spectrum of a fluorescence (fluorescent component (the same hereinafter)) directly (without multiple reflections within the integrating sphere) in the second state and correct the spectrum of the fluorescence detected in the first state according to the spectrum of the fluorescence detected in the second state. Hence, this quantum-yield measurement device can measure the quantum yield of the sample accurately and efficiently.

The movement mechanism may have a stage having the integrating sphere secured thereto, a nut fastened to the stage, a feed screw shaft in threaded engagement with the nut, and a drive source for rotating the feed screw shaft. This can smoothly move the integrating sphere within the dark box.

Here, in first and second regions extending from the light entrance opening to the light exit opening in the stage as seen axially of the feed screw shaft, the nut may be secured to the first region having a shorter distance from the light entrance opening to the light exit opening. This allows the light entrance and exit openings to oppose the light exit and entrance parts, respectively, with favorable precision.

The movement mechanism may further have a sleeve secured to the stage and a guide shaft inserted through the sleeve. This can move the integrating sphere more smoothly within the dark box.

Here, a sample table for supporting another sample may be detachably attached to the integrating sphere, and the sleeve may be secured to the second region so as to oppose the feed screw shaft with the light entrance opening or light exit opening interposed therebetween as seen axially of the guide shaft. This makes it easier to have access to the integrating sphere from the opposite sides of the light entrance and exit openings when the guide shaft opposes the feed screw shaft with the light entrance and exit openings interposed therebetween, respectively, whereby the sample table can easily be attached to and detached from the integrating sphere.

The device may further comprise a position detector for detecting first position of the integrating sphere in the first state and second position of the integrating sphere in the second state, and the movement mechanism may stop the integrating sphere when the first or second position is detected by the position detector. This can securely reproduce each of the first and second states where the sample container of the sample cell is located inside and outside of the integrating sphere, respectively.

The light exit opening may be provided with a first stop member for narrowing the light to be measured, and the light entrance part may be provided with a second stop member for narrowing the light to be measured. Thus providing the stop members in two stages can make the light to be measured incident on the light detection unit at an appropriate angle, so as to prevent stray light from occurring within the light detection unit. Providing the light exit opening of the integrating sphere with the first stop member can prevent foreign substances from entering the integrating sphere through the light exit opening.

Advantageous Effects of Invention

The present invention can measure the quantum yield of the sample accurately and efficiently.

BRIEF DESCRIPTION OF DRAWINGS

FIG. 8 is a set of diagrams for explaining the method of measuring the quantum yield by using the quantum-yield measurement device of FIG. 1.

DESCRIPTION OF EMBODIMENTS

Figure 1:
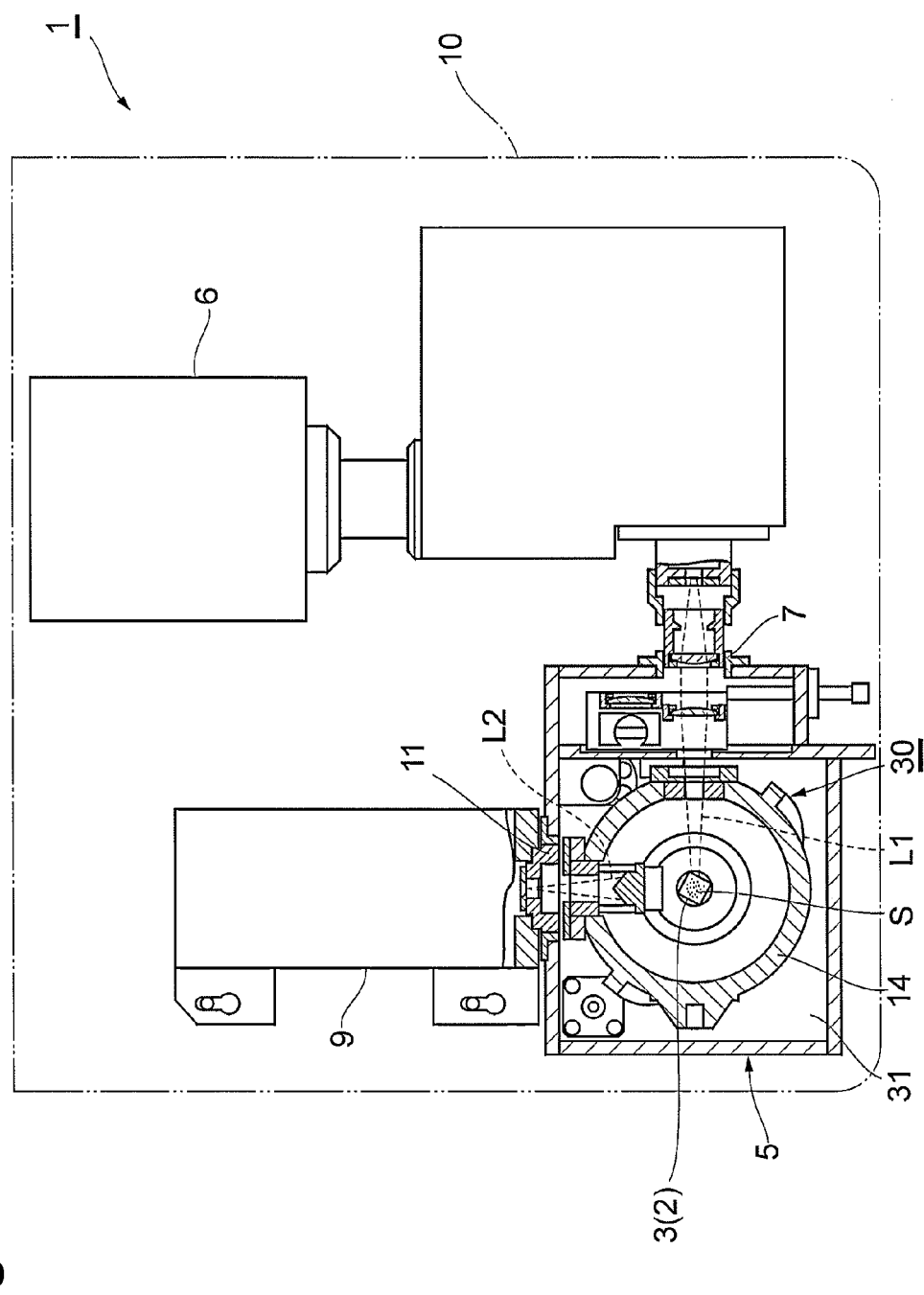
FIG. 1 is a plan view of the quantum-yield measurement device in accordance with an embodiment of the present invention.

In the following, preferred embodiments of the present invention will be explained in detail with reference to the drawings. In the drawings, the same or equivalent parts will be referred to with the same signs while omitting their overlapping descriptions.

Figure 2:
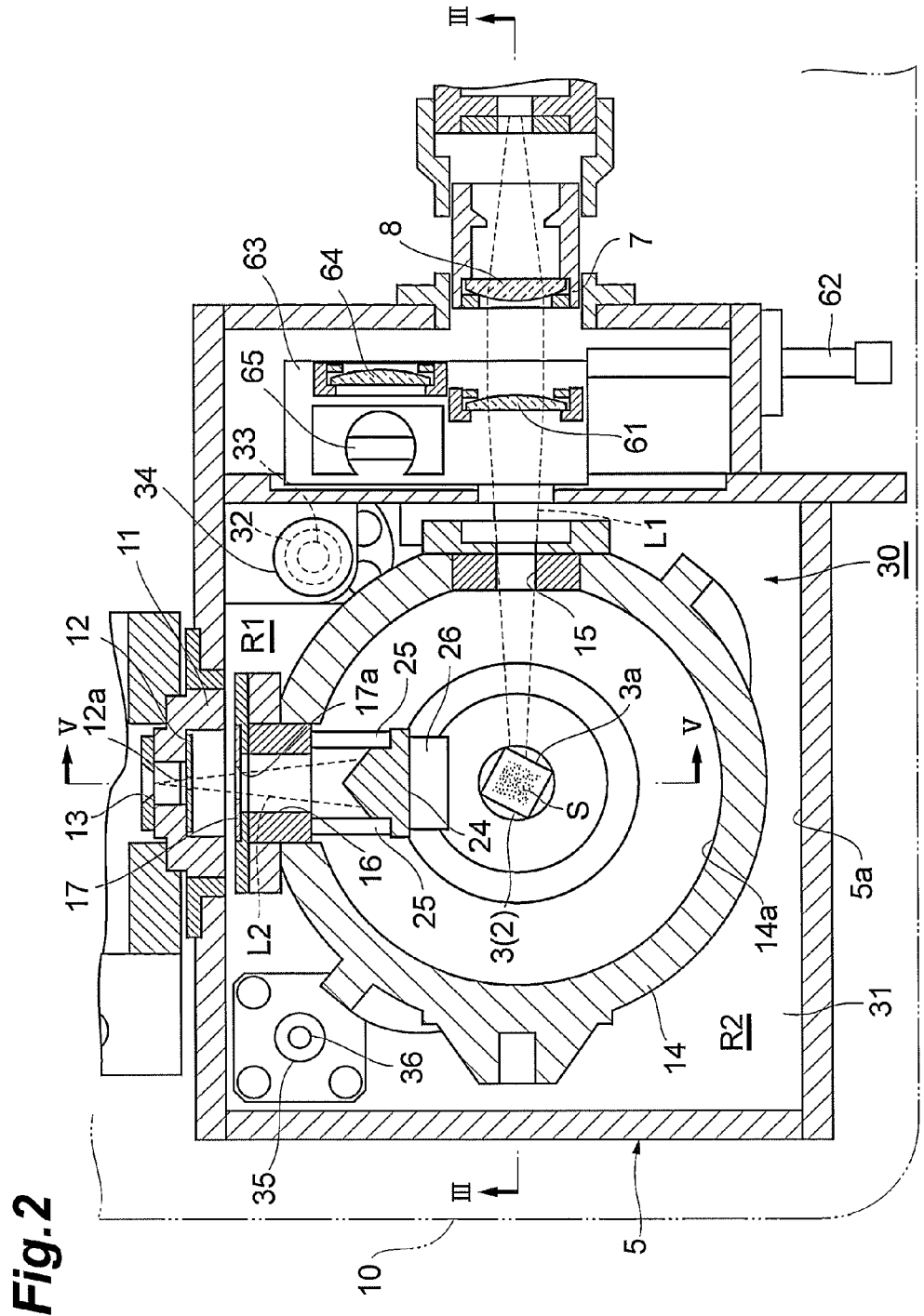
FIG. 2 is an enlarged view of the inside of a dark box of FIG. 1 and its surrounding parts.

FIG. 1 is a plan view of the quantum-yield measurement device in accordance with an embodiment of the present invention, while FIG. 2 is an enlarged view of the inside of a dark box of FIG. 1 and its surrounding parts. As FIGS. 1 and 2 illustrate, the quantum-yield measurement device 1 is a device for measuring a quantum yield (light-emitting quantum yield, fluorescent quantum yield, phosphorescence quantum yield, or the like) of a sample S by irradiating a sample container 3 of a sample cell 2 for containing the sample S with pumping light L1 and detecting light to be measured L2 emitted from at least one of the sample S and sample container 3. An example of the sample S is one in which a light-emitting material or the like used for a light-emitting device such as that of organic EL is dissolved in a predetermined solvent. The sample cell 2 is made of synthetic silica, for example, while the sample container 3 is a quadrangular prism vessel, for example.

The quantum-yield measurement device 1 is equipped with a dark box 5 for arranging therein the sample container 3. The dark box 5 is a rectangular parallelepiped box made of a metal and blocks light from entering from the outside. The dark box 5 has an inner surface 5a coated with a material which absorbs the pumping light L1 and the light to be measured L2, and so forth.

A light exit part 7 of a light generation unit 6 is connected to one side wall of the dark box 5. The light generation unit 6 is a pumping light source constituted by a xenon lamp, a spectroscope, and the like, for example, and generates the pumping light L1. The pumping light L1 is collimated by a lens 8 provided with the light exit part 7, so as to enter the dark box 5.

A light entrance part 11 of a light detection unit 9 is connected to a rear wall of the dark box 5. The light detection unit 9 is a multichannel detector constituted by a spectroscope, a CCD sensor, or the like, for example, and detects the light to be measured L2. The light to be measured L2 is narrowed by an opening 12a which is an aperture of a stop member (second stop member) 12 provided with the light entrance part 11, so as to enter the light detection unit 9 through a slit 13.

An integrating sphere 14 is arranged within the dark box 5. The integrating sphere 14 has an inner surface 14a coated with a highly diffusive reflecting agent such as barium sulfate or is formed from a material such as PTFE or Spectralon. The integrating sphere 14 is formed with a light entrance opening 15 for the pumping light L1 to enter and a light exit opening 16 for the light to be measured L2 to exit. The pumping light L1 is converged by a lens 61 within the dark box 5, so as to enter the integrating sphere 14 through the light entrance opening 15. The light to be measured L2 is narrowed by an opening 17a which is an aperture of a stop member (first stop member) 17 provided with the light exit opening 16, so as to be emitted out of the integrating sphere 14.

The foregoing dark box 5, light generation unit 6, and light detection unit 9 are contained in a housing 10 made of a metal. The optical axis of the pumping light L1 emitted from the light exit part 7 of the light generation unit 6 and the optical axis of the light to be measured L2 made incident on the light entrance part 11 of the light detection unit 9 are substantially orthogonal to each other within a horizontal plane.

Figure 3:
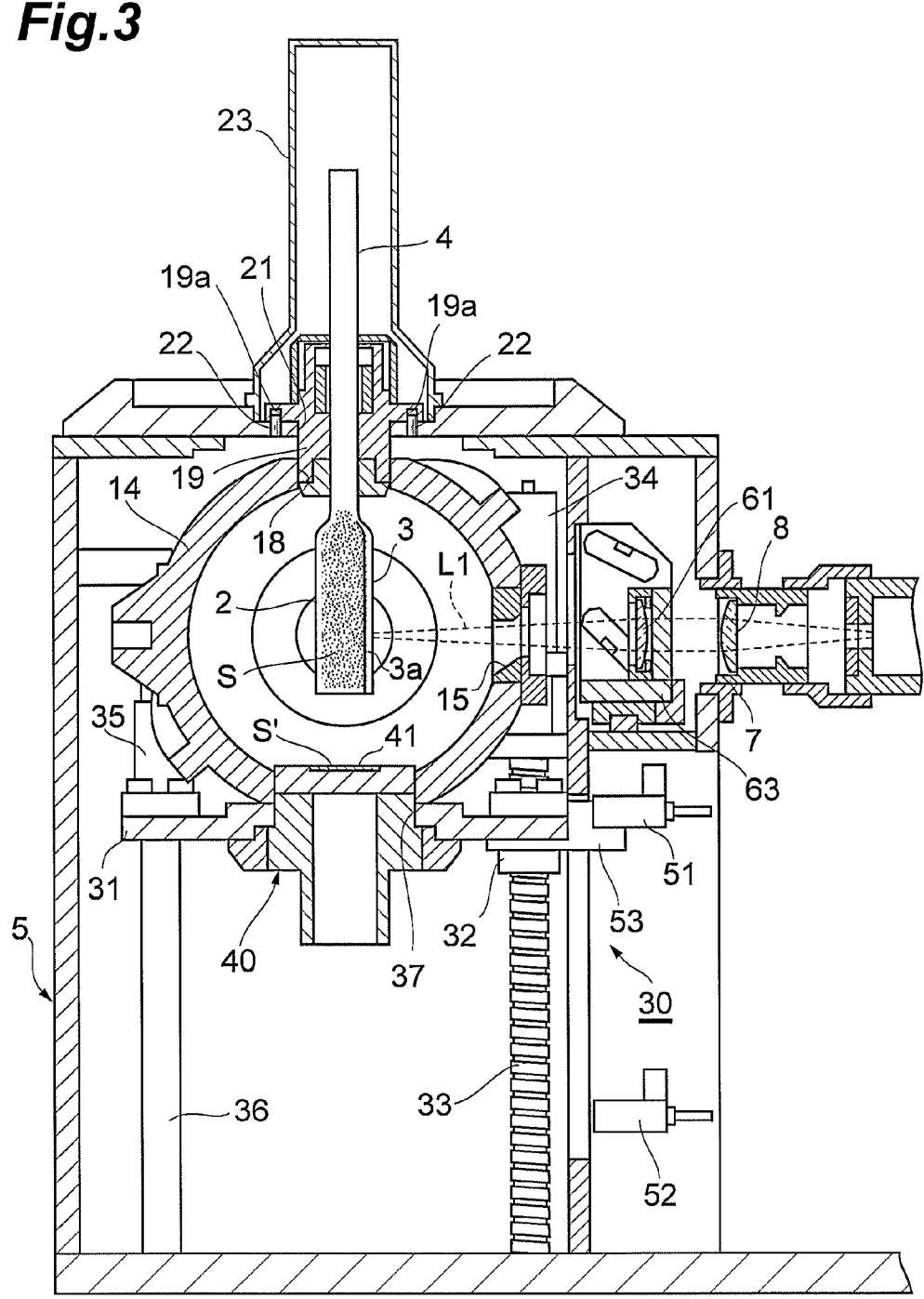
FIG. 3 is a sectional view taken along the line III-III of FIG. 2.

FIG. 3 is a sectional view taken along the line of FIG. 2. As FIG. 3 illustrates, a cell insertion opening 18 for inserting therethrough the sample cell 2 is formed in the upper part of the integrating sphere 14, while an opening 21 is formed in the upper wall of the dark box 5 so as to oppose the cell insertion opening 18. The sample cell 2 has a branch pipe 4 extending from the sample container 3, while the branch pipe 4 is held with a sample holder 19 which is partly arranged within the openings 18, 21. A flange part of the sample holder 19 is formed with a pair of positioning holes 19a, into which a pair of positioning pins 22 provided at the upper wall of the dark box 5 so as to hold the opening 21 therebetween are fitted, respectively. This tilts a side face 3a of the sample container 3 at a predetermined angle other than 90° with respect to the optical axis of the pumping light L1 in such a state as to suppress rattling and prevents the pumping light L1 reflected by the side face 3a from returning to the light exit part 7. A light-shielding cover 23 is mounted on the upper wall of the dark box 5 so as to cover the branch pipe 4 of the sample cell 2, the sample holder 19, and the opening 21.

The quantum-yield measurement device 1 further comprises a movement mechanism 30 for moving the integrating sphere 14 within the dark box 5. The movement mechanism 30 moves the integrating sphere 14 such that the sample container 3 attains each of a first state of being located inside of the integrating sphere 14 and a second state of being located outside of the integrating sphere 14. The movement mechanism 30 causes the light entrance opening 15 and light exit opening 16 of the integrating sphere 14 to oppose the light exit part 7 of the light generation unit 6 and the light entrance part 11 of the light detection unit 9, respectively, in the first state.

The movement mechanism 30 has a stage 31 having the integrating sphere 14 secured thereto, a nut 32 fastened to the stage 31, a feed screw shaft 33 in threaded engagement with the nut 32, and a motor (drive source) 34 for rotating the feed screw shaft 33. The feed screw shaft 33 extends vertically within the dark box 5 and has a lower end part rotatably supported by the lower wall of the dark box 5. The motor 34 is connected to the upper end part of the feed screw shaft 33 and secured to the dark box 5. Balls are incorporated in the nut 32, so that the nut 32 and the feed screw shaft 33 constitute a ball screw.

The movement mechanism 30 further has a sleeve 35 secured to the stage 31 and a guide shaft 36 inserted through the sleeve 35. The guide shaft 36 extends vertically within the dark box 5 and has upper and lower end parts secured to the dark box 5. The sleeve 35 is slidable with respect to the guide shaft 36 axially thereof.

When seen axially of the feed screw shaft 33 as illustrated in FIG. 2, in regions (first and second regions) R1, R2 extending from the light entrance opening 15 of the integrating sphere 14 to the light exit opening 16 thereof in the stage 31, the nut 32 is secured to the region R1 having a shorter distance from the light entrance opening 15 of the integrating sphere 14 to the light exit opening 16 thereof. When seen axially of the guide shaft 36, the sleeve 35 is secured to the region R2 so as to oppose the feed screw shaft 33 with the light exit opening 16 of the integrating sphere 14 interposed therebetween.

Returning to FIG. 3, the quantum-yield measurement device 1 further comprises a position detector 51 for detecting a first position of the integrating sphere 14 in the first state where the sample container 3 is located inside of the integrating sphere 14 and a position detector 52 for detecting a second position of the integrating sphere 14 in the second state where the sample container 3 is located outside of the integrating sphere 14. Examples of the position detectors 51, 52 include photointerrupters which respectively detect the first and second positions when a light-shielding plate 53 secured to the stage 31 is located between their corresponding light-emitting and -receiving parts. When the first or second position is detected by the position detectors 51, 52, the movement mechanism 30 stops the integrating sphere 14.

Figure 4:
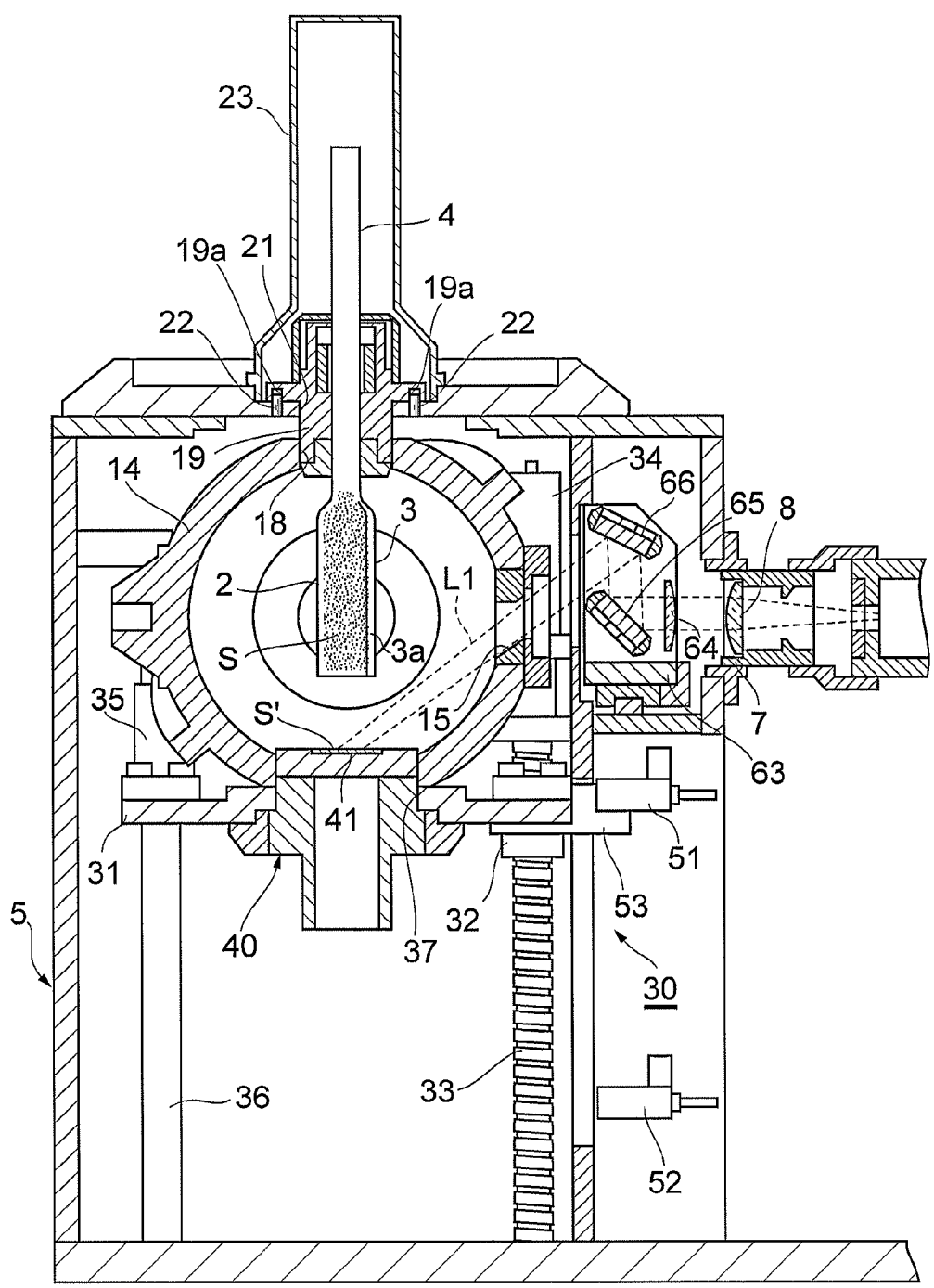
FIG. 4 is a sectional view in a state where another sample is irradiated with pumping light.

FIG. 4 is a sectional view in a state where another sample is irradiated with pumping light. As FIG. 4 illustrates, the lower part of the integrating sphere 14 and the stage 31 are formed with an opening 37. A sample table 40 detachably attached to the stage 31 from the lower side thereof is partly arranged in the opening 37. That is, the sample table 40 is detachably attached to the integrating sphere 14. The sample table 40 is used for supporting a sample (another sample) S' such as a powder or solid formed into a thin film on a substrate 41 such as glass. There is a case where the sample S' is mounted on the sample table 40 while being contained in a vessel such as a Petri dish.

When irradiating the sample S' with the pumping light L1, a handle (optical path switching means) 62 (see FIG. 2) moves the stage 63, so as to switch from the lens 61 to a lens 64. The pumping light L1 converged by the lens 64 is sequentially reflected by mirrors 65, 66, so as to irradiate the sample S'. Here, the optical axis of the pumping light L1 tilts at a predetermined angle other than 90° with respect to the surface of the substrate 41 and thus prevents the pumping light L1 reflected by the surface of the substrate 41 from returning to the light exit part 7. The light entrance opening 15 of the integrating sphere 14 is formed into such a shape that the pumping light L1 is not blocked thereby when irradiating any of the samples S and S'. Since the light entrance opening 15 of the integrating sphere 14 is thus formed so as to be greater on the outside than inside of the integrating sphere 14, the pumping light L1 is not blocked even when the optical path is switched by the handle (optical path switching means) 62.

Figure 5:
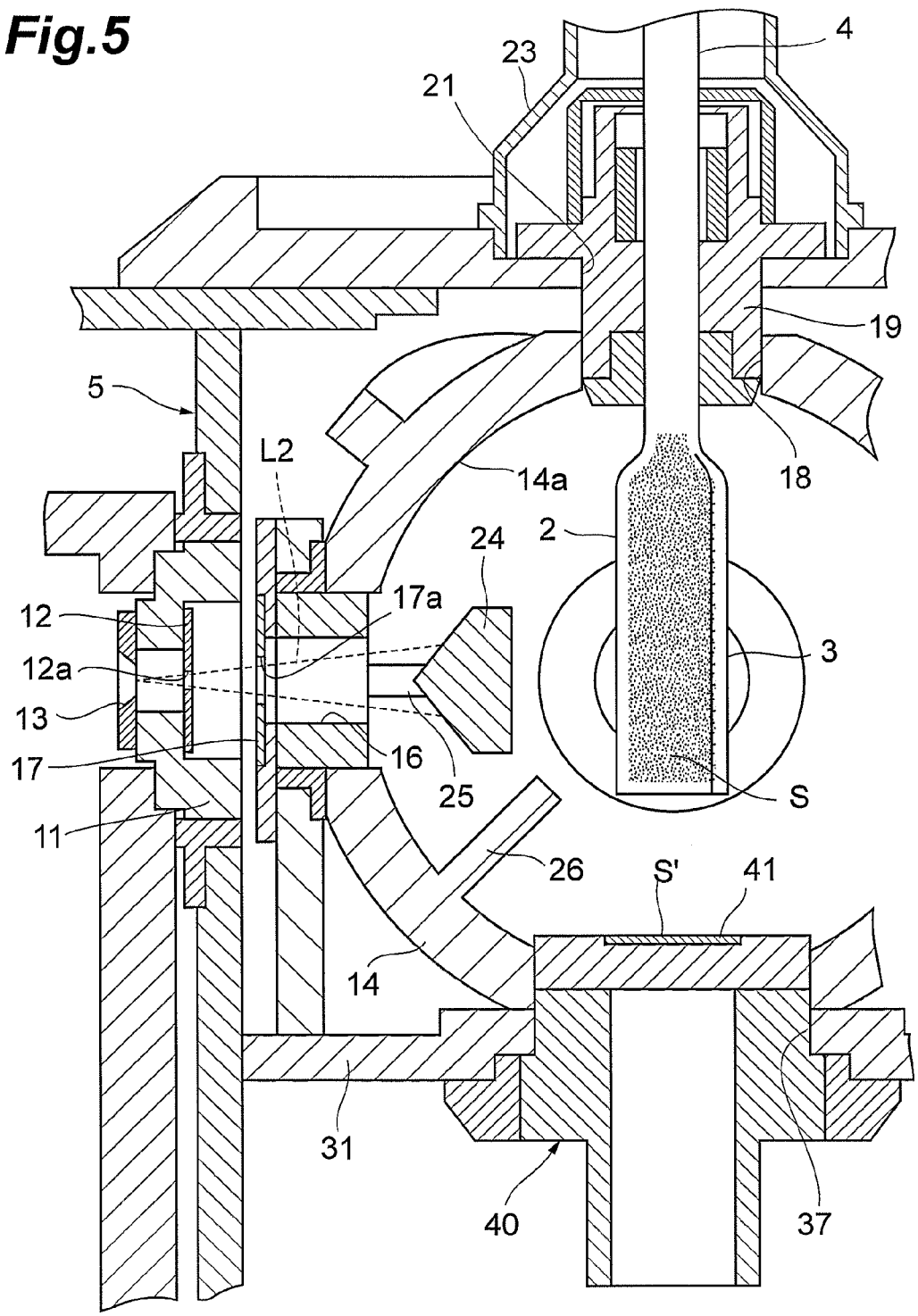
FIG. 5 is a sectional view taken along the line V-V of FIG. 2.

FIG. 5 is a sectional view taken along the line V-V of FIG. 2. As FIG. 5 illustrates, a baffle 24 arranged within the integrating sphere 14 at a position opposing the light exit opening 16. The baffle 24 is supported by a support pole 25 erected on the inner surface 14a of the integrating sphere 14. A baffle 26 is integrally formed with the inner surface 14a of the integrating sphere 14. The baffle 24 prevents the light to be measured L2 emitted from the sample S and sample container 3 from directly entering the light entrance part 11 of the light detection unit 9, while the baffle 26 prevents the light to be measured L2 emitted from the sample S' from directly entering the light entrance part 11 of the light detection unit 9.

Figure 6:
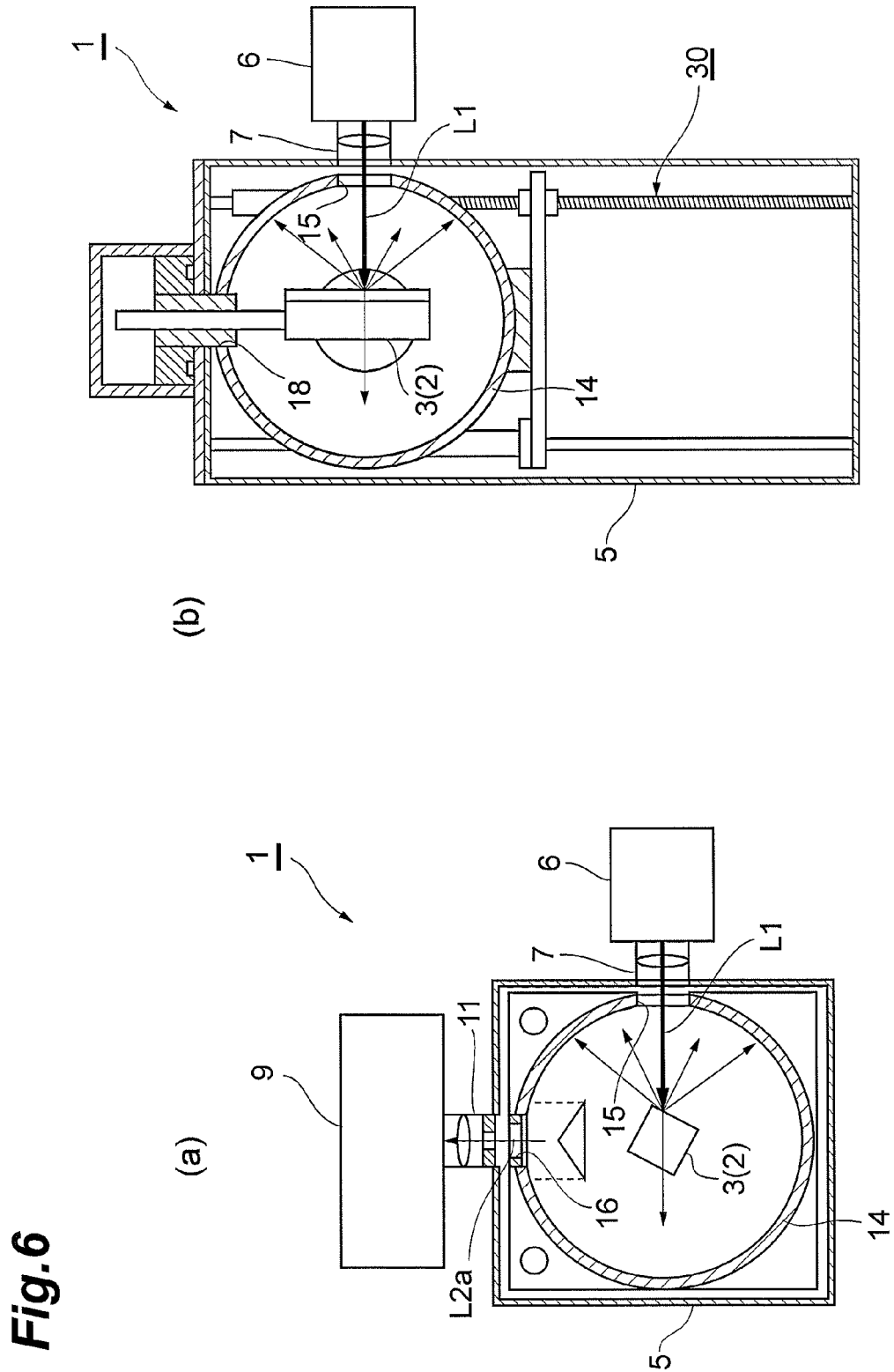
FIG. 6 is a set of diagrams for explaining a method of measuring a quantum yield by using the quantum-yield measurement device of FIG. 1.
Figure 7:
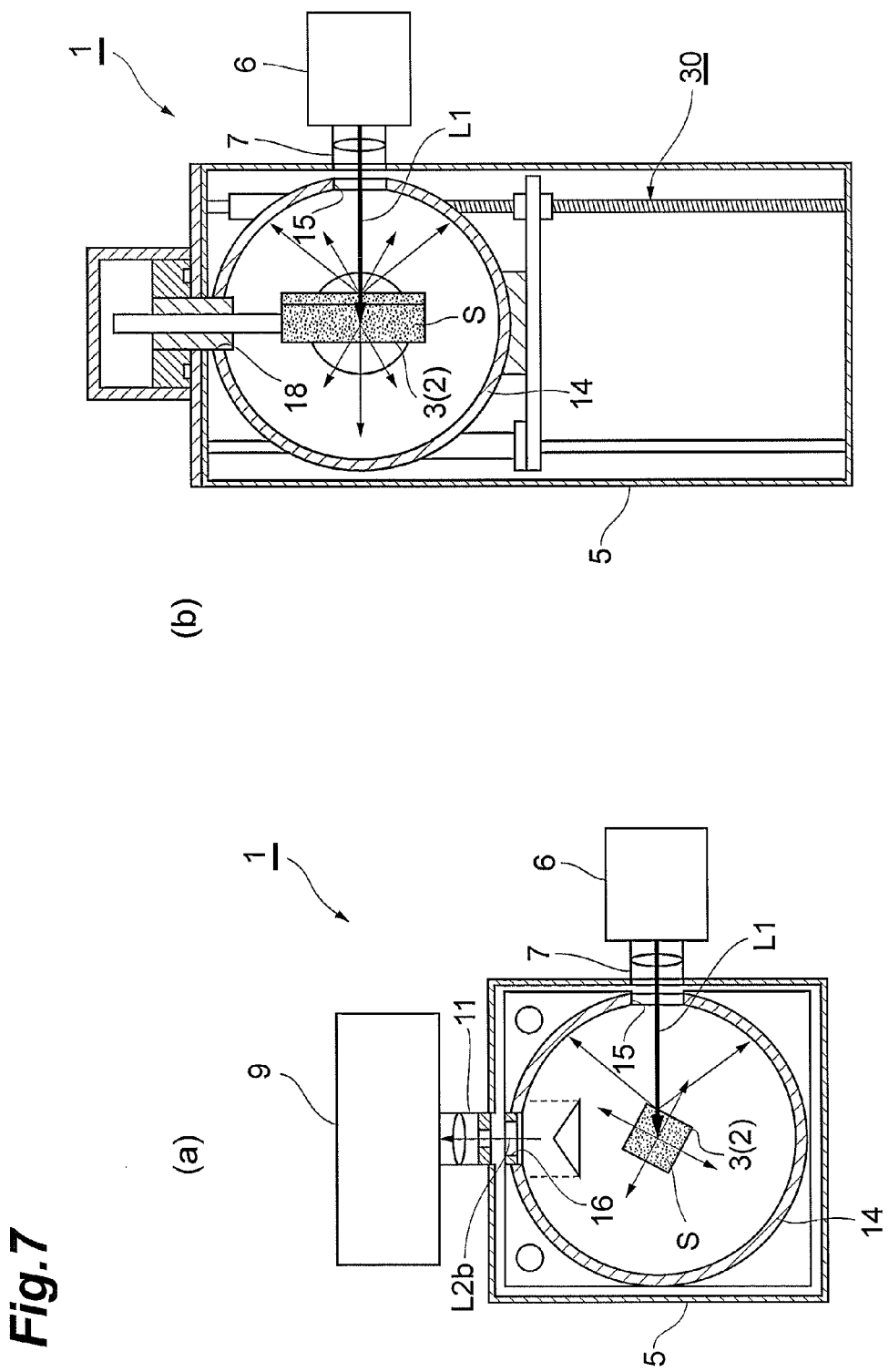
FIG. 7 is a set of diagrams for explaining the method of measuring the quantum yield by using the quantum-yield measurement device of FIG. 1.

A method of measuring a quantum yield by using thus constructed quantum-yield measurement device 1 will now be explained. In FIGS. 6 to 8, (a) and (b) are transverse and longitudinal sectional views of the inside of the dark box.

First, as FIG. 6 illustrates, an empty sample cell 2 not containing the sample S is set into the dark box 5. Subsequently, the sample container 3 in the first state of being located inside of the integrating sphere 14 is irradiated with the pumping light L1 emitted from the light generation unit 6. The parts of pumping light L1 reflected by and transmitted through the sample container 3 incur multiple reflections, so as to be detected by the light detection unit 9 as light to be measured L2a emitted from the sample container 3.

Next, as FIG. 7 illustrates, the sample cell 2 contains the sample S and is set into the dark box 5. Then, the sample container 3 in the first state of being located inside of the integrating sphere 14 is irradiated with the pumping light L1 emitted from the light generation unit 6. The part of pumping light L1 reflected by the sample container 3 and the fluorescence generated by the sample S incur multiple reflections within the integrating sphere 14, so as to be detected by the light detection unit 9 as light to be measured L2b emitted from the sample S and sample container 3.

Subsequently, as FIG. 8 illustrates, the movement mechanism 30 moves (down, here) the integrating sphere 14 such that the sample container 3 attains the second state of being located outside of the integrating sphere 14. Along with such a change from the first state to the second state, the light entrance opening 15 and light exit opening 16 of the integrating sphere 14 move relative to the light exit part 7 of the light generation unit 6 and the light entrance part 11 of the light detection unit 9, respectively. In the second state, the sample container 3 is irradiated with the pumping light L1 emitted from the light generation unit 6. The fluorescence generated by the sample S is detected directly (without multiple reflections within the integrating sphere 14) by the light detection unit 9 as light to be measured L2c emitted from the sample S.

Figure 9:
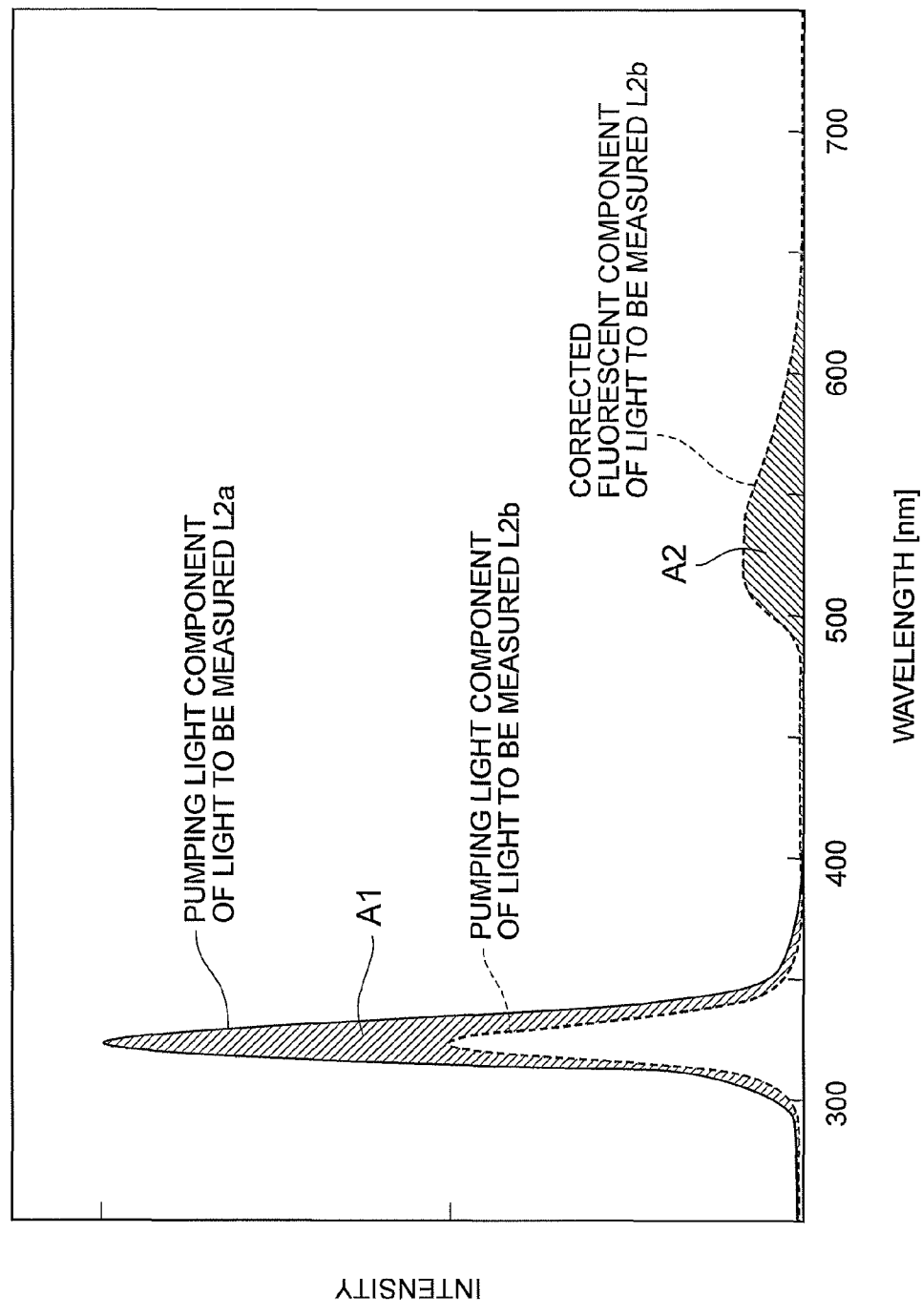
FIG. 9 is a graph for explaining the method of measuring the quantum yield by using the quantum-yield measurement device of FIG. 1.

When data of the light to be measured L2a, L2b, L2c are acquired as in the foregoing, a data analyzer such as a personal computer computes the number of photons (a value corresponding to the number of photons such as a value in proportion to the number of photons (the same hereinafter))

of pumping light L1 absorbed by the sample S according to data of the pumping light components of light to be measured L2a, L2b. The number of photons of pumping light L1 absorbed by the sample S corresponds to area A1 in FIG. 9.

On the other hand, the data analyzer corrects data of the fluorescent component of light to be measured L2b according to the data of light to be measured L2c (see Non Patent Literature 1 for details). As a consequence, even when the sample S is optically absorptive with respect to the fluorescent component, so that reabsorption occurs, the data analyzer computes the number of photons of fluorescence corrected so as to become the true number (i.e., the number of photons of the fluorescence actually emitted from the sample S). The number of photons of fluorescence emitted from the sample S corresponds to area A2 in FIG. 9.

Then, the data analyzer computes the quantum yield of the sample S, which is the ratio of "the number of photons of fluorescence emitted from the sample S" to "the number of photons of pumping light absorbed by the sample S." There is also a case where a solvent not dissolving the sample S therein is contained in the sample cell 2, which is set into the dark box 5, so that the light to be measured L2a is detected in the first state.

In the quantum-yield measurement device 1, as explained in the foregoing, the movement mechanism 30 moves the integrating sphere 14 within the dark box 5 such that the sample container 3 of the sample cell 2 attains each of the first and second states of being located inside and outside of the integrating sphere 14, respectively. This makes it possible to detect the number of photons of fluorescence directly (without multiple reflections within the integrating sphere 14) in the second state and correct the number of photons of fluorescence detected in the first state according to the number of photons of fluorescence detected in the second state. Hence, the quantum-yield measurement device 1 can measure the quantum yield of the sample S accurately and efficiently.

The movement mechanism 30 has the stage 31 having the integrating sphere 14 secured thereto, the nut 32 fastened to the stage 31, the feed screw shaft 33 in threaded engagement with the nut 32, and the motor 34 for rotating the feed screw shaft 33. The movement mechanism 30 further has the sleeve 35 secured to the stage 31 and the guide shaft 36 inserted through the sleeve 35. These make it possible for the integrating sphere 14 to move smoothly within the dark box 5.

When seen axially of the feed screw shaft 33, in regions R1, R2 extending from the light entrance opening 15 to the light exit opening 16 in the stage 31, the nut 32 is secured to the region R1 having a shorter distance from the light entrance opening 15 to the light exit opening 16. This allows the light entrance opening 15 and light exit opening 16 to oppose the light exit part 7 of the light generation unit 6 and the light entrance part 11 of the light detection unit 9, respectively, with favorable precision in the first state where the sample container 3 of the sample cell 2 is located inside of the integrating sphere 14.

When seen axially of the guide shaft 36, the sleeve 35 is secured to the region R2 so as to oppose the feed screw shaft 33 with the light exit opening 16 interposed therebetween. This makes it easier to have access to the integrating sphere 14 from the opposite side of the light exit opening 16 (i.e., the front wall side of the dark box 5), whereby the sample table 40 can easily be attached to and detached from the integrating sphere 14.

When the first or second position is detected by the position detectors 51, 52, the movement mechanism 30 stops the integrating sphere 14. This can securely reproduce each of the first and second states where the sample container 3 of the sample cell 2 is located inside and outside of the integrating sphere 14, respectively.

The light exit opening 16 of the integrating sphere 14 is provided with the stop member 17 for narrowing the light to be measured L2, while the light entrance part 11 of the light detection unit 9 is provided with the stop member 12 for narrowing the light to be measured L2. Thus providing the stop members 17, 12 in two stages (and separating them for the light exit opening 16 of the integrating sphere 14 and the light entrance part 11 of the light detection unit 9 and attaining a longer distance between the stop members 17, 12, thereby allowing the stop member 12 to make the opening 12a relatively small) can make the light to be measured L2 incident on the light detection unit 9 at an appropriate angle, so as to prevent stray light from occurring within the light detection unit 9. Further, providing the light exit opening 16 of the integrating sphere 14 with the stop member 17 can prevent foreign substances from entering the integrating sphere 14 through the light exit opening 16. This is effective in particular when moving the integrating sphere 14 as in the quantum-yield measurement device 1, since a gap occurs between the inner surface 5a of the dark box 5 and the light exit opening 16 of the integrating sphere 14. Preferably, the opening 17a of the stop member 17 has a size smaller than that of the opening 12a of the stop member 12.

The sample holder 19 is only mounted on the upper wall of the dark box 5 in a state where the positioning pins 22 are fitted in the positioning holes 19a, and the light-shielding cover 23 is similarly just mounted on the upper wall of the dark box 5. As a consequence, any force exerted on the sample cell 2 when the integrating sphere 14 rises can escape, thereby preventing the sample cell 2 and the like from being damaged.

The present invention is not limited to one embodiment thereof explained in the foregoing. For example, the sleeve 35 may be secured to the region R2 so as to oppose the feed screw shaft 33 with the light entrance opening 15 of the integrating sphere 14 interposed therebetween when seen axially of the guide shaft 36. This makes it easier to have access to the integrating sphere 14 from the opposite side of the light entrance opening 15 (i.e., the other side wall side of the dark box 5), whereby the sample table 40 can easily be attached to and detached from the integrating sphere 14.

The light entrance part 11 of the light detection unit 9 may be provided with a plurality of stop members 12 of the light detection unit 9 without the stop member 17 for the light exit opening 16 of the integrating sphere 14. This allows the light to be measured L2 to enter the light detection unit 9 under substantially the same condition between the first and second states where the sample container 3 of the sample cell 2 is located inside and outside of the integrating sphere 14, respectively. The light generation unit 6 and the dark box 5 may optically be connected to each other with an optical fiber or the like, and so may the light detection unit 9 and the dark box 5. The housing 10 may be constructed as a dark box.

INDUSTRIAL APPLICABILITY

The present invention can measure the quantum yield of the sample accurately and efficiently.

REFERENCE SIGNS LIST

1 . . . quantum-efficiency measurement device; 2 . . . sample cell; 3 . . . sample container; 5 . . . dark box; 6 . . . light generation unit; 7 . . . light exit part; 9 . . . light detection unit; 11 . . . light entrance part; 12 . . . stop member (second stop member); 14 ... integrating sphere; 15 ... light entrance opening; 16 ... light exit opening; 17 ... stop member (first stop member); 30 ... movement mechanism; 31 ... stage; 32 ... nut; 33 ... feed screw shaft; 34 ... motor (drive source); 35 ... sleeve; 36 ... guide shaft; 40 ... sample table; 51, 52 ... position detector; L1 ... pumping light; L2, L2a, L2b, L2c ... light to be measured; R1 ... region (first region); R2 ... region (second region); S ... sample; S' ... sample (another sample)

The invention claimed is:

1. A quantum-yield measurement device for measuring a quantum yield of a sample by irradiating a sample container of a sample cell for containing the sample with pumping light and detecting light to be measured emitted from at least one of the sample and sample container, the device comprising:
   a dark box configured to arrange therein the sample container;
   a light generation unit, having a light exit part connected to the dark box, configured to generate the pumping light;
   a light detection unit, having a light entrance part connected to the dark box, configured to detect the light to be measured;
   an integrating sphere, arranged within the dark box, having a light entrance opening for the pumping light to enter and a light exit opening for the light to be measured to exit; and
   a movement mechanism configured to move the integrating sphere such that the sample container attains each of a first state of being located inside of the integrating sphere and a second state of being located outside of the integrating sphere, and to cause the light entrance opening to oppose the light exit part and causing the light exit opening to oppose the light entrance part, in the first state.

2. A quantum-yield measurement device according to claim 1, wherein the movement mechanism has a stage having the integrating sphere secured thereto, a nut fastened to the stage, a feed screw shaft in threaded engagement with the nut, and a drive source configured to rotate the feed screw shaft.

3. A quantum-yield measurement device according to claim 2, wherein, in first and second regions extending from the light entrance opening to the light exit opening in the stage as seen axially of the feed screw shaft, the nut is secured to the first region having a shorter distance from the light entrance opening to the light exit opening.

4. A quantum-yield measurement device according to claim 2, wherein the movement mechanism further has a sleeve secured to the stage and a guide shaft inserted through the sleeve.

5. A quantum-yield measurement device according to claim 4, wherein a sample table configured to support another sample is detachably attached to the integrating sphere; and
   wherein the sleeve is secured to the second region so as to oppose the feed screw shaft with the light entrance opening or light exit opening interposed therebetween as seen axially of the guide shaft.

6. A quantum-yield measurement device according to claim 1, further comprising a position detector configured to detect first position of the integrating sphere in the first state and second position of the integrating sphere in the second states; and
   wherein the movement mechanism stops the integrating sphere when the first or second position is detected by the position detector.

7. A quantum-yield measurement device according to claim 1, wherein the light exit opening is provided with a first stop member configured to narrow the light to be measured; and
   wherein the light entrance part is provided with a second stop member for narrowing configured to narrow the light to be measured.

* * * * *